United States Patent
Arambulo

[11] Patent Number: 6,027,219
[45] Date of Patent: Feb. 22, 2000

[54] EAR MIRROR

[76] Inventor: Robert J. Arambulo, 16203 Skagway St., Whittier, Calif. 90603

[21] Appl. No.: 09/095,969

[22] Filed: Jun. 11, 1998

[51] Int. Cl.[7] .................................................. G02B 7/182
[52] U.S. Cl. .......................... 359/872; 359/873; 359/874; 359/875; 248/475.1
[58] Field of Search ..................... 359/872, 873, 359/874, 875, 876; D6/300–314; D24/139; D28/64.1; 248/475.1

[56] References Cited

U.S. PATENT DOCUMENTS

| | | | |
|---|---|---|---|
| D. 261,845 | 11/1981 | Wachtel | D6/233 |
| 5,359,461 | 10/1994 | Rice et al. | 359/874 |
| 5,611,362 | 3/1997 | Duncan et al. | 132/301 |
| 5,798,881 | 8/1998 | Mazurek et al. | 359/872 |

FOREIGN PATENT DOCUMENTS 1098313  1/1968  United Kingdom .

*Primary Examiner*—Cassandra Spyrou
*Assistant Examiner*—Mohammad Y. Sikder

[57] ABSTRACT

A new ear mirror for permitting self-examination of an ear by a user. The inventive device includes a handle and a reflective member. A pivot arm is outwardly extended from the reflective member and is pivotally coupled to the handle.

13 Claims, 3 Drawing Sheets

EAR MIRROR

BACKGROUND OF THE INVENTION

1. Field of the Invention

The present invention relates to mirror devices and more particularly pertains to a new ear mirror for permitting self-examination of an ear by a user.

2. Description of the Prior Art

The use of mirror devices is known in the prior art. More specifically, mirror devices heretofore devised and utilized are known to consist basically of familiar, expected and obvious structural configurations, notwithstanding the myriad of designs encompassed by the crowded prior art which have been developed for the fulfillment of countless objectives and requirements.

Known prior art mirror devices include U.S. Pat. No. Des. 309,833; U.S. Pat. No. 3,730,612; U.S. Pat. No. 5,052,925; U.S. Pat. No. 5,458,486; U.S. Pat. No. 5,428,484; and U.S. Pat. No. 3,164,904.

While these devices fulfill their respective, particular objectives and requirements, the aforementioned patents do not disclose a new ear mirror. The inventive device includes a handle and a reflective member. A pivot arm is outwardly extended from the reflective member and is pivotally coupled to the handle.

In these respects, the ear mirror according to the present invention substantially departs from the conventional concepts and designs of the prior art, and in so doing provides an apparatus primarily developed for the purpose of permitting self-examination of an ear by a user.

SUMMARY OF THE INVENTION

In view of the foregoing disadvantages inherent in the known types of mirror devices now present in the prior art, the present invention provides a new ear mirror construction wherein the same can be utilized for permitting self-examination of an ear by a user.

The general purpose of the present invention, which will be described subsequently in greater detail, is to provide a new ear mirror apparatus and method which has many of the advantages of the mirror devices mentioned heretofore and many novel features that result in a new ear mirror which is not anticipated, rendered obvious, suggested, or even implied by any of the prior art mirror devices, either alone or in any combination thereof.

To attain this, the present invention generally comprises a handle and a reflective member. A pivot arm is outwardly extended from the reflective member and is pivotally coupled to the handle.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new ear mirror apparatus and method which has many of the advantages of the mirror devices mentioned heretofore and many novel features that result in a new ear mirror which is not anticipated, rendered obvious, suggested, or even implied by any of the prior art mirror devices, either alone or in any combination thereof.

It is another object of the present invention to provide a new ear mirror which may be easily and efficiently manufactured and marketed.

It is a further object of the present invention to provide a new ear mirror which is of a durable and reliable construction.

An even further object of the present invention is to provide a new ear mirror which is susceptible of a low cost of manufacture with regard to both materials and labor, and which accordingly is then susceptible of low prices of sale to the consuming public, thereby making such ear mirror economically available to the buying public.

Still yet another object of the present invention is to provide a new ear mirror which provides in the apparatuses and methods of the prior art some of the advantages thereof, while simultaneously overcoming some of the disadvantages normally associated therewith.

Still another object of the present invention is to provide a new ear mirror for permitting self-examination of an ear by a user.

Yet another object of the present invention is to provide a new ear mirror which includes a handle and a reflective member. A pivot arm is outwardly extended from the reflective member and is pivotally coupled to the handle.

Still yet another object of the present invention is to provide a new ear mirror that lets a user see a reflection of the inside of their ears for personal hygiene.

Even still another object of the present invention is to provide a new ear mirror that is used in combination with another mirror so that a user may view the inside of their ear.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be made to the accompanying drawings and descriptive matter in which there are illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein.

DESCRIPTION OF THE PREFERRED EMBODIMENT

Figure 1:
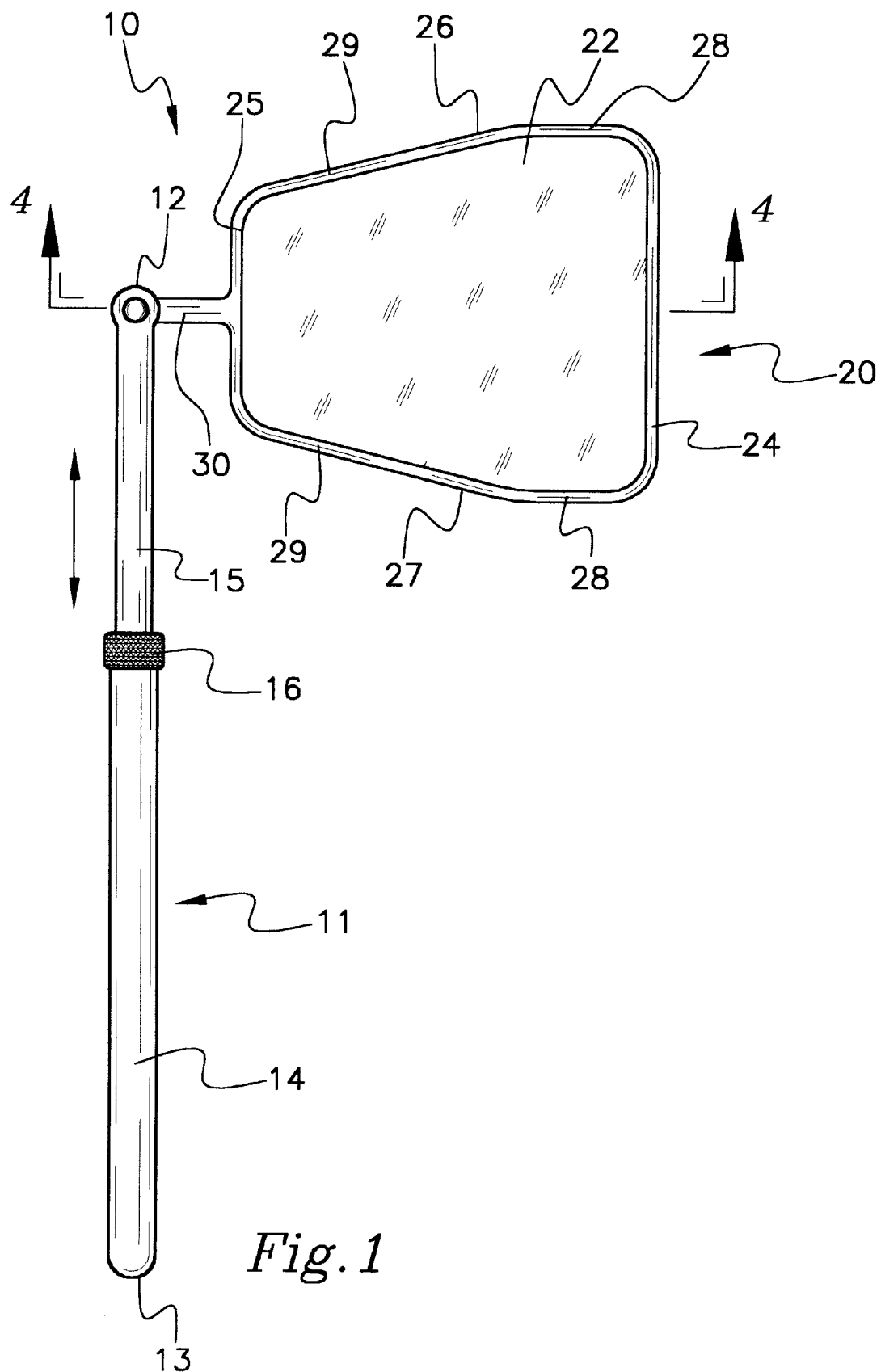
FIG. 1 is a schematic first side view of a new ear mirror according to the present invention.
Figure 2:
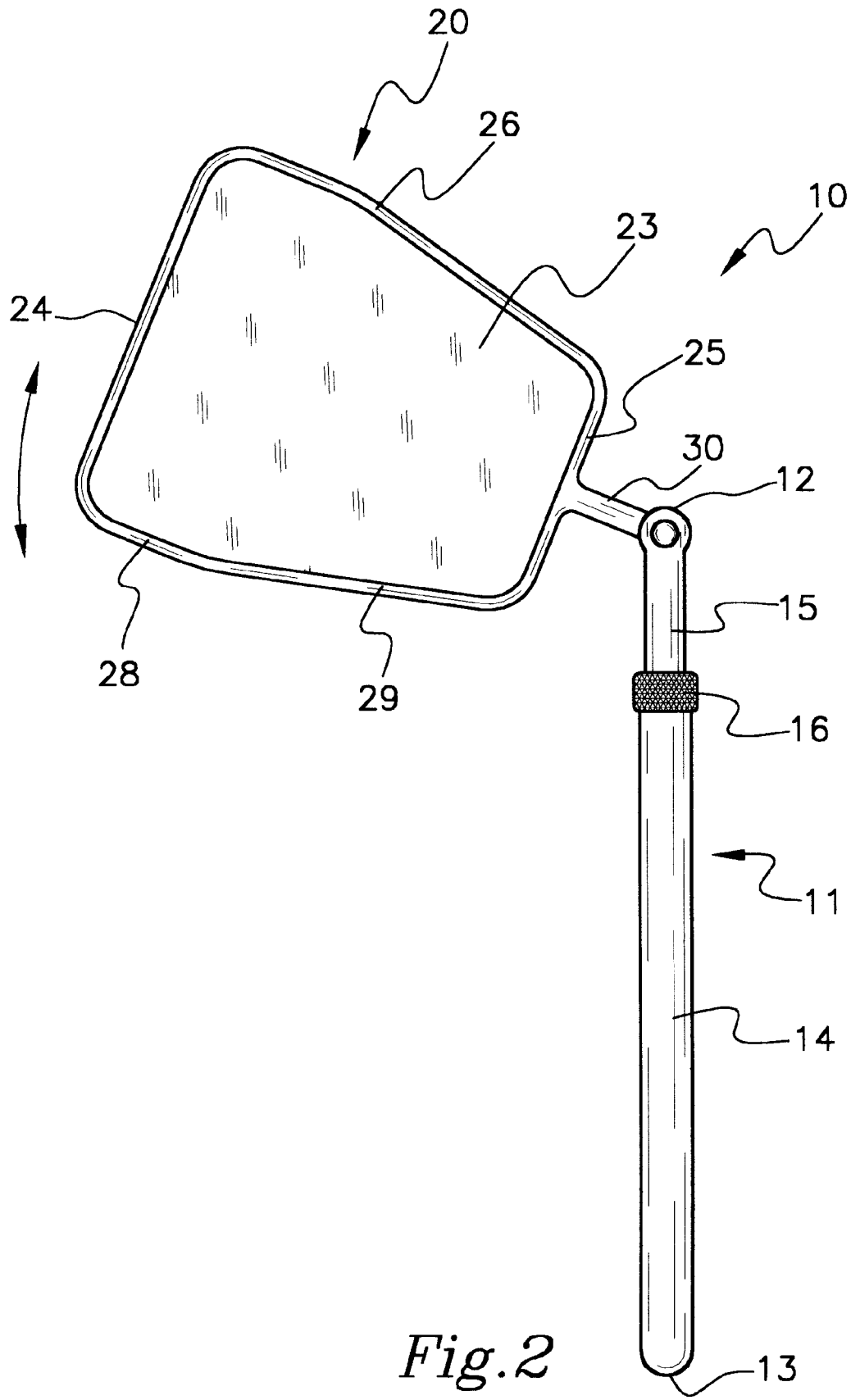
FIG. 2 is a schematic second side view of the present invention.
Figure 3:
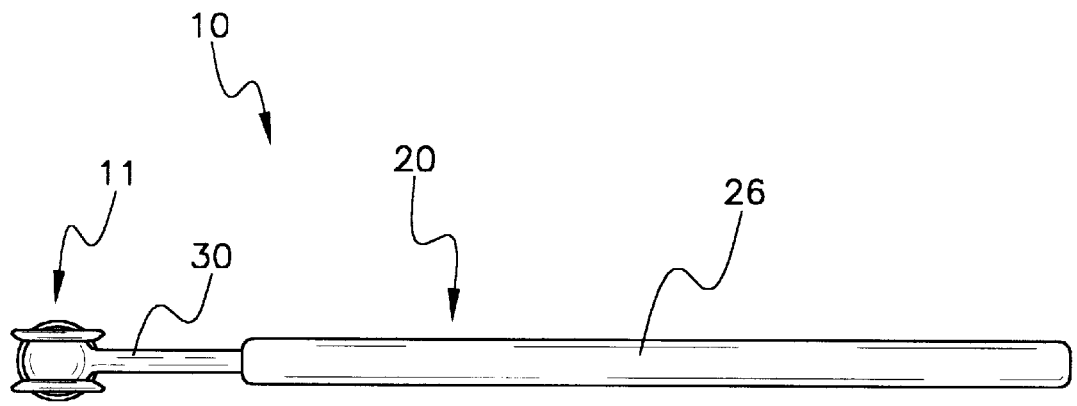
FIG. 3 is a schematic top side view of the present invention.
Figure 4:
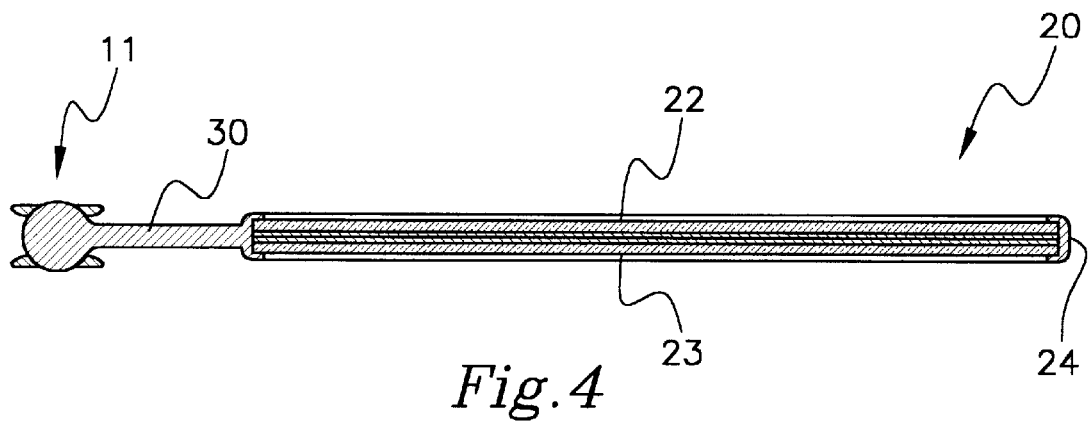
FIG. 4 is a schematic sectional view of the present invention taken from line 4—4 on FIG. 1.

With reference now to the drawings, and in particular to FIGS. 1 through 5 thereof, a new ear mirror embodying the principles and concepts of the present invention and generally designated by the reference numeral 10 will be described.

As best illustrated in FIGS. 1 through 5, the ear mirror 10 generally comprises a handle 11 and a reflective member 20. A pivot arm 30 is outwardly extended from the reflective member 20 and is pivotally coupled to the handle 11.

Figure 5:
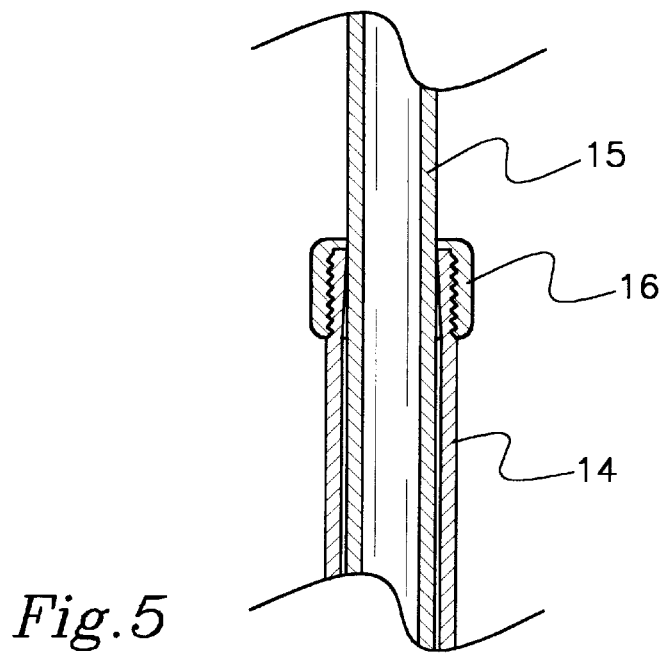
FIG. 5 is a schematic partial sectional view of the handle of the present invention.

In closer detail, the elongate handle 11 has a pair of opposite proximal and distal ends 12,13 and a length extending between the proximal and distal ends 12,13 of the handle 11. Preferably, the handle 11 is telescopically extendible along the length of the handle 11. In this preferred embodiment, the handle 11 has tubular elongate first and second portions 14,15 with the first portion 14 of the handle 11 telescopically receiving the second portion 15 of the handle 11. The first portion 14 of the handle 11 is located towards the distal end 13 of the handle 11 while the second portion 15 of the handle 11 is located towards the proximal end 12 of the handle 11. As best illustrated in FIG. 5, a threaded holding nut 16 is threadedly attached to the first portion 14 of the handle 11. The threaded holding nut 16 is designed for releasably holding the second portion 15 of the handle 11 in a fixed position with respect to first portion 14 of the handle 11.

The reflective member 20 has first and second surfaces 22,23. The first and second surfaces 22,23 of the reflective member 20 each comprises a light reflective mirror. Preferably, each of the mirrors comprises magnifying mirrors such as concave reflecting mirror so that the image reflected by the mirror is enlarged. The reflective member 20 also has opposite first and second end edges 24,25 and a pair of side edges 26,27 extending between the first and second end edges 24,25. Each of the side edges 26,27 of the reflective member 20 has first and second regions 28,29, the first regions 28 of the side edges 26,27 are positioned towards the first end edge 24 of the reflective member 20. The second regions 29 of the side edges 26,27 are positioned towards the second end edge 25 of the reflective member 20. The first regions 28 of the side edges 26,27 are generally parallel with each other while the second regions 29 of the side edges 26,27 converge towards the second end edge 25 of the reflective member 20.

In an ideal embodiment, the reflective member 20 has a length defined between the first and second end edges 24,25 of the reflective mirror which is less than about two-fifths the length of the handle 11. Also ideally, the length of the second end edge 25 of the reflective member 20 is less than one half the length of the first end edge 24 of the reflective member 20. Additionally, the length of the first regions 28 of the side edges 26,27 is ideally less than about one third the length of the second regions 28,29 of the side edges 26,27. In an ideal illustrative embodiment, the length of the handle 11 is less than about 10 inches, the length of the reflective member 20 is less than about 4 inches and a thickness defined between the first and second surfaces 22,23 of the reflective member 20 of less than about ¼ inch.

A pivot arm 30 is outwardly extended from the second end edge 25 of the reflective member 20 so that the length of the pivot arm 30 is extended substantially perpendicular to the length of the second side edge of the reflective member 20. The pivot arm 30 is pivotally coupled to the proximal end 12 of the handle 11 to permit pivoting of the reflective member 20 with respect to the handle 11. Preferably, the reflective member 20, the pivot arm 30 and the handle 11 lie in a common plane.

In use, a user extends the handle to a desired length. The pivot arm is pivoted so that the reflective member is extended from the handle at the desired angle. The reflective member is positioned against the back of an ear of the user. The user then faces another mirror to view the reflection of the inside the user's ear from one of the mirrored surfaces of the reflective member.

As to a further discussion of the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described and accordingly, all suitable modifications and equivalents may be resorted to, falling within the scope of the invention.

I claim:

1. A device, comprising:

an elongate handle having a pair of opposite proximal and distal ends and a length extending between said proximal and distal ends of said handle;

a reflective member having first and second surfaces, opposite first and second end edges and a pair of side edges extending between said first and second end edges of said reflective member;

a pivot arm being outwardly extended from said second end edge of said reflective member;

said pivot arm being pivotally coupled to said proximal end of said handle;

said first and second surfaces of said reflective member each comprising a mirror;

wherein each of said side edges of said reflective member has first and second regions;

said first regions of said side edges being positioned towards said first end edge of said reflective member, said second regions of said side edges being positioned towards said second end edge of said reflective member;

said first regions of said side edges being generally parallel with each other; and said second regions of said side edges converging towards said second end edge of said reflective member.

2. The device of claim 1, wherein said handle is telescopically extendible along said length of said handle.

3. The device of claim 2, wherein said handle has elongate first and second portions, said first portion of said handle telescopically receiving said second portion of said handle, said first portion of said handle being located towards said distal end of said handle, said second portion of said handle being located towards said proximal end of said handle.

4. The device of claim 3, further comprising a threaded holding nut being threadedly attached to said first portion of said handle, said threaded holding nut being for releasably holding said second portion of said handle in a position with respect to first portion of said handle.

5. The device of claim 1, wherein the length of said pivot arm is extended substantially perpendicular to the length of said second side edge of said reflective member.

6. The device of claim 1, wherein each of said mirrors comprises magnifying mirrors.

7. The device of claim 1, wherein said reflective member, said pivot arm and said handle lie in a common plane.

8. The device of claim 1, wherein said reflective member has a length defined between said first and second end edges of said reflective mirror, wherein said length of said reflective member is less than about two-fifths said length of said handle.

9. The device of claim 8, wherein said length of said handle is less than about 10 inches, and wherein said length of said reflective member is less than about 4 inches.

10. The device of claim 1, wherein said reflective member has a thickness defined between said first and second surfaces of said reflective member of less than about ¼ inch.

11. The device of claim 1, wherein the length of said second end edge of said reflective member is less than one half the length of said first end edge of said reflective member.

12. The device of claim 1, wherein the length of said first regions of said side edges being less than about one third the length of said second regions of said side edges.

13. A device, comprising:

an elongate handle having a pair of opposite proximal and distal ends and a length extending between said proximal and distal ends of said handle;

wherein said handle is telescopically extendible along said length of said handle, said handle having elongate first and second portions, said first portion of said handle telescopically receiving said second portion of said handle, said first portion of said handle being located towards said distal end of said handle, said second portion of said handle being located towards said proximal end of said handle;

a threaded holding nut being threadedly attached to said first portion of said handle, said threaded holding nut being for releasably holding said second portion of said handle in a position with respect to first portion of said handle;

a reflective member having first and second surfaces, opposite first and second end edges and a pair of side edges extending between said first and second end edges of said reflective member;

a pivot arm being outwardly extended from said second end edge of said reflective member, the length of said pivot arm being extended substantially perpendicular to the length of said second side edge of said reflective member;

said pivot arm being pivotally coupled to said proximal end of said handle;

said first and second surfaces of said reflective member each comprising a mirror, wherein each of said mirrors comprises magnifying mirrors;

wherein said reflective member, said pivot arm and said handle lie in a common plane;

wherein said length of said handle is less than about 10 inches;

wherein said reflective member has a length defined between said first and second end edges of said reflective mirror, wherein said length of said reflective member is less than about two-fifths said length of said handle, wherein said length of said reflective member is less than about 4 inches;

wherein said reflective member has a thickness defined between said first and second surfaces of said reflective member of less than about ¼ inch;

wherein the length of said second end edge of said reflective member is less than one half the length of said first end edge of said reflective member;

wherein each of said side edges of said reflective member has first and second regions, said first regions of said side edges being positioned towards said first end edge of said reflective member, said second regions of said side edges being positioned towards said second end edge of said reflective member, said first regions of said side edges being generally parallel with each other, said second regions of said side edges converging towards said second end edge of said reflective member; and the length of said first regions of said side edges being less than about one third the length of said second regions of said side edges.

* * * * *